(12) United States Patent
Fredriksson (10) Patent No.: US 8,013,134 B2
(45) Date of Patent: Sep. 6, 2011

(54) KIT FOR PROXIMITY PROBING WITH MULTIVALENT PROXIMITY PROBES

(75) Inventor: Simon Fredriksson, Uppsala (SE)

(73) Assignee: Olink AB, Uppsala (SE)

( * ) Notice: Subject to any disclaimer, the term of this patent is extended or adjusted under 35 U.S.C. 154(b) by 1049 days.

(21) Appl. No.: 10/496,385

(22) PCT Filed: Nov. 22, 2002

(86) PCT No.: PCT/SE02/02133
§ 371 (c)(1),
(2), (4) Date: May 24, 2004

(87) PCT Pub. No.: WO03/044231
PCT Pub. Date: May 30, 2003

(65) Prior Publication Data
US 2005/0003361 A1    Jan. 6, 2005

(30) Foreign Application Priority Data

| Nov. 23, 2001 | (SE) | .................................. 0103905-6 |
| Apr. 12, 2002 | (SE) | .................................. 0201140-1 |

(51) Int. Cl.
| C07H 21/02 | (2006.01) |
| C07H 21/04 | (2006.01) |
| C12Q 1/68 | (2006.01) |
| C12P 19/34 | (2006.01) |
| G01N 33/00 | (2006.01) |

(52) U.S. Cl. .................... 536/23.1; 536/24.3; 536/24.33; 435/6; 435/91.1; 435/91.2; 435/91.52; 435/810; 436/94

(58) Field of Classification Search ................ 435/6, 7.1, 435/91.1, 183, 810; 436/94; 536/23.1, 24.3, 536/24.33, 25.3; 530/3, 300, 350; 424/130.1, 424/178.1, 184.1
See application file for complete search history.

(56) References Cited

U.S. PATENT DOCUMENTS

| 4,833,084 | A | * | 5/1989 | Carrico | .................... 530/388.21 |
| 5,543,332 | A |   | 8/1996 | Lihme et al. | |
| 5,747,252 | A | * | 5/1998 | Yang et al. | .......................... 435/6 |
| 5,900,461 | A |   | 5/1999 | Harris | |
| 2002/0028450 | A1 | * | 3/2002 | Greene et al. | ..................... 435/6 |
| 2002/0182609 | A1 | * | 12/2002 | Arcot | ................................ 435/6 |

FOREIGN PATENT DOCUMENTS

WO        WO 01/61037 A1      8/2001

OTHER PUBLICATIONS

Attached definition of "multivalent". Printed on Aug. 4, 2008.*

Stratagene Catalog (1988), p. 39. Published by Stratgene, 11011 North Torrey Pines Road, La Jolla, CA 92037, USA.*
Gibson, Ursula et al., "A Novel Method for Real Time Quantitative RT-PCR", Genome Research, vol. 6, pp. 995-1001, 1996.
Boder, Eric T. et al., "Directed evolution of antibody fragments with monovalent femtomolar antigen-binding affinity", PNAS, vol. 97, No. 20, pp. 10701-10705, Sep. 26, 2000.
Mourez, Michael et al., "Designing a polyvalent inhibitor of anthrax toxin", Nature Biotechnology, vol. 19, pp. 958-961, Oct. 2001.
Rao, Jianghong et al., "A Trivalent System from Vancomycin D-Ala-D-Ala with Higher Affinity Than Avidin-Biotin", Science, vol. 280, pp. 708-711, May 1, 1998.
Barlow, E. et al., "Antibody Molecules", Antibodies: A Laboratory Manual, pp. 7-35, Chapters 2 & 3, Cold Spring Harbor Laboratory Press, 1998.
Maeda, Mizuo et al., "Psoralen-Containing Vinyl Monomer for Conjugation of Double-Helical DNA with Vinyl Polymers", Bioconjugate Chem., vol. 5, No. 6, pp. 527-531, 1994.
Minard-Basquin, Claire et al., "Oligonucleotide-Polymer Conjugates: Effect of the Method of Synthesis on Their Structure and Performance in Diagnostic Assays", Bioconjugate Chem., vol. 11, No. 6, pp. 795-804, 2000.
Luo, Yi, "Hyaluronic Acid-*N*-hydroxysuccinimide: A Useful Intermediate for Bioconjugation", Bioconjugate Chem., vol. 12, No. 6, pp. 1085-1088, 2001.
Baner, Johan et al., "Signal amplification of padlock probes by rolling circle replication", Nucleic Acid Research, vol. 26, no. 22, pp. 5073-5078, 1998.
Niemeyer, Christof M. et al., "Nanostructured DNA-Protein Aggregates Consisting of Covalent Oligonucleotide-Streptavidin Conjugates", Bioconjugate Chem., vol. 12, No. 3, pp. 364-371, 2001.
Niemeyer, Christof M. et al., "Oligonucleotide-directed self assembly of proteins: semisynthetic DNA-streptavidin hybrid molecules as connectors for the generation of macroscopic arrays and the construction of supramolecular bioconjugates", Nucleic Acids Research, vol. 22, No. 25, pp. 5530-5539, 1994.
Niemeyer, Christof M. et al., "Self-assembly of DNA-streptavidin nanostructures and their use as reagents in immuno-PCR", Nucleic Acids Research, vol. 27, No. 23, pp. 4553-4561, 1999.
Causey et al., Detection of low affinity interactions between peptides and heat shock proteins by chemiluminescence of enhanced avidity reactions (Clear), Nature Biotechnology, 14:348-351 (1996).

(Continued)

*Primary Examiner* — Frank W Lu
(74) *Attorney, Agent, or Firm* — Browdy and Neimark, PLLC (57) ABSTRACT

The present invention relates to sensitive, rapid and convenient assays for detection and or quantification of one or more analyte(s) in solution using multivalent proximity probes. The proximity probes each comprise several binding moieties, such as antibodies, and associated nucleic acid(s). When the binding moieties have bound to their analyte(s), the nucleic acids on opposite proximity probes interact with each other and a signal is generated based on this interaction. The multivalent proximity probes are especially valuable for highly sensitive and specific protein detection.

18 Claims, 4 Drawing Sheets

OTHER PUBLICATIONS

Soukka et al., Supersensitive time-resolved immunofluorometric assay of free prostate-specific antigen with nanoparticle label technology, Clinical Chemistry, 47(7):1269-1278 (2001).

Soukka et al., Utilization of kinetically enhanced monovalent binding affinity by immunoassays based on multivalent nanoparticle-antibody bioconjugates, Analytical Chemistry, 73(10):2254-2260 (2001).

Yoshitani et al., Microscale synthesis of dextran-based multivalent N-linked oligosaccharide probes, Analytical Biochemistry, 277:127-134 (2000).

* cited by examiner

KIT FOR PROXIMITY PROBING WITH MULTIVALENT PROXIMITY PROBES

FIELD OF THE INVENTION

The present invention is within the medical field. More precisely, the invention relates to sensitive, rapid and convenient assays for detection and or quantification of one or more analyte(s) in solution using multivalent proximity probes.

BACKGROUND

Proximity probing (also termed proximity ligation) is a technique capable of detecting the nearness of the two so called proximity probes and is used for specific, sensitive and rapid detection of macromolecules such as proteins. A proximity probe consists of a binding moiety (with specific affinity for the target molecule) and a thereto-coupled reactive nucleic acid. The probes usually work in pairs, each with a coupled nucleic acid capable of interacting with the other one (usually through ligation) when these are in proximity of each other. These nucleic acids are sometimes referred to as reactive nucleic acids. The proximity between the probes is provided when two probes bind their respective binding sites on a target analyte. This proximity enables the two nucleic acids coupled to the probes to interact with one another and give rise to a new nucleic acid sequence, which is easily detected and quantified by amplification. Real time fluorometric PCR (1) is usually used for detection with the primers placed one on each of the nucleic acid sequences. Homogenous proximity probing using monovalent proximity probes, performed in solution with no washing steps, is described in patent application WO 01/61037.

An assay is performed by first incubating the proximity probe pair with the sample containing the analyte to allow complexes to form. A mixture is then added containing the appropriate reagents for allowing the nucleic acids to interact and then amplifying the reaction product. In the case of interaction through ligation and subsequent PCR amplification the mixture contains ligase enzyme, ATP, hybridization template also referred to as splint or ligation template, PCR primers, dNTP's, DNA polymerase, and TaqMan probe for real-time detection. Several types of proximity dependent interactions between the reactive nucleic acids can be used and some examples of these are described in WO 01/61037.

SUMMARY OF THE INVENTION

When performing a proximity-probing assay in solution with a monovalent proximity probe pair, it was found that the sensitivity of the assay is directly dependent on the affinity of the binding moieties of the proximity probes. The probes must be added to the assay at a low concentration in order to not give rise to too much background ligation since the efficiency of ligation of the reactive nucleic acids is dependent on their relative concentration. Target binding of the probes provides a locally high concentration, which drives the ligation reaction resulting in the signal, but if the probes are added to the assay at a too high concentration, the background rises and assay sensitivity is decreased.

In an optimal assay as many of the target analytes as possible are bound by two proximity probes to ensure a high signal while the probe concentration is kept at a minimum ensuring low background. The degree of binding is determined by the affinity of the probes for their binding site on the target analyte. The dissociation constant, $K_d$, for the probe-target interaction gives a measure of at what concentration 50% of the binding sites have bound a probe according to the following formula:

P=probe concentration
B=Binding site concentration
PB=probe/binding site complex concentration $$Kd=((P)*(B))/(PB)=((P-PB)*(B-PB))/(PB)$$

When using proximity probes of low affinity (high $K_d$ value) towards its target protein few targets will be bound by probes. In homogenous proximity probing two binders are necessary to bind the target protein and if both of these have a low affinity this combined loss will be great. Table one gives some examples of simulated efficiencies of binding with various $K_d$'s of the two binding moieties with 10 pM target analyte (containing site A and B) and 20 pM of the proximity probes of equal affinity toward their respective binding sites. The probability of two proximity probes having bound one and the same target analyte is the square of the probability of binding one probe. Thereby, low affinity proximity probes will give low assay sensitivity.

TABLE 1

Binding efficiencies depend on affinity

| Kd | % bound Site A | % bound Site B | % bound Site A & B |
|---|---|---|---|
| 100 nM | 0.02 | 0.02 | 0.000004 |
| 10 nM | 0.2 | 0.2 | 0.0004 |
| 1 nM | 2 | 2 | 0.04 |
| 0.1 nM | 16 | 16 | 2.4 |

Figure 1:
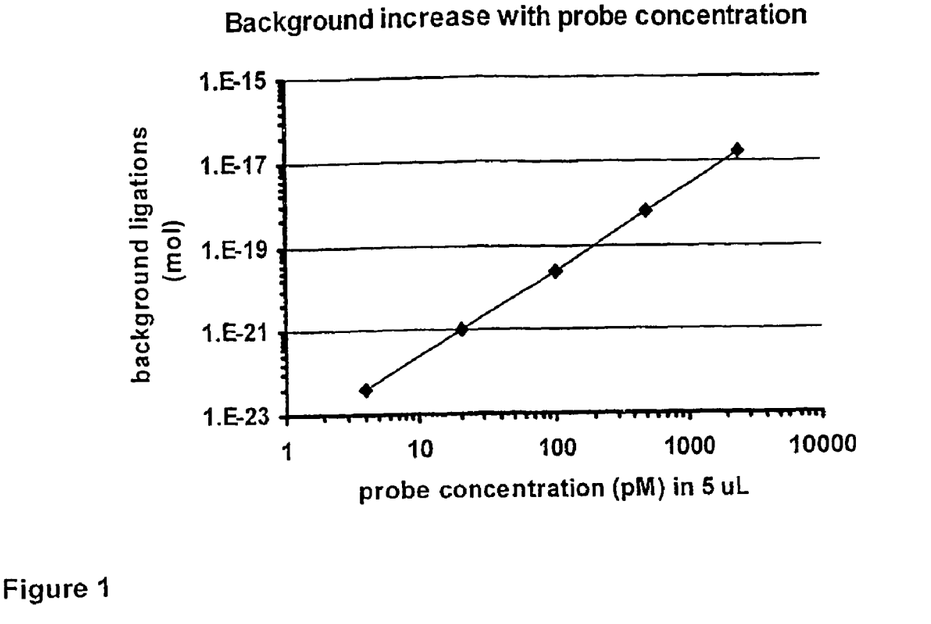
FIG. 1) Simulation of increase in background signal with increased use of proximity probe concentration.

The problem with low affinity probes can not be overcome by adding a higher concentration of the probes since the background will then dramatically increase. For example; if the concentration of both of the proximity probes is increased from 20 pM to 100 pM (5 fold increases) to yield a higher degree of target binding, the background ligation will increase 25 fold (5×5) since the efficiency of the background ligation is dependent on the concentration of both probes. The ligation reaction behaves as a pseudo second order reaction in which efficiency depends on the concentrations of the two reactants, the proximity probes. FIG. 1 shows some simulated data on the increase in background with five fold increases in proximity probe concentration.

The international patent application WO 01/61037 gives one solution to this problem by adding a high concentration of the low affinity proximity probes and then diluting the sample. However, this will also decrease the signal as well as the background.

In many cases it will be difficult to obtain binding moiety components (such as antibodies) of the proximity probes with sufficiently high affinity for its target analyte to ensure an assay of high sensitivity. With the above reasoning regarding the need for two binding events per analyte for detection, a calculation for a 1 nM Kd antibody pair (very good affinity for antibodies) would yield a 100 fold lower sensitivity compared to the binding moieties used in monovalent proximity probing described in the examples of WO 01/61037.

Antibodies of very high affinity, and also other affinity reagents, are of general interest. Several attempts have been made to increase the affinity of an antibody by for example in vitro maturation. These procedures have at times been successful but are very laborious and time consuming (2).

The present invention disclosed here provides a new solution to the problem with low affinity proximity probe reagents by directly addressing the affinity of the proximity probe.

This invention provides means to increase the affinity of proximity probes through multivalency, also providing an easier way to purify the proximity-probes during manufacture.

Thus, in a first aspect the invention relates to a method for detecting and/or quantifying one or more analyte(s) in solution, characterised by a) binding of two or more multivalent proximity probes to a respective binding site on said analyte(s), wherein the multivalent proximity probes are comprised of at least two binding moieties preferably between 2 and 100, linked by a flexible linker and a thereto associated nucleic acid, also sometimes referred to as a reactive nucleic acid, b) allowing the binding moieties to bind to the several copies of the analyte(s) and allowing the nucleic acids to interact with each other if they are in close proximity to each other; and c) detection and/or quantification of the degree of interaction between the nucleic acids.

The binding moieties may be specific for the same or different sites on the analyte.

The nucleic acid may be coupled to the binding moiety or somewhere else on the proximity probe, for example on the polymer backbone, see below.

The binding moieties of the multivalent proximity probes are selected from an antibody, antibody fragment, protein, nucleic acid, such as an aptamer, soluble cell surface receptor, combinatorially derived protein from phage display or ribosome display or combinations thereof as well as any chemical functionality reactive with the analyte specific binding moiety.

In one embodiment, the binding moieties are biotinylated and incubated with streptavidin-oligonucleotide conjugates before step a) in the method of the invention.

The analytes may be bio-molecules for example proteins, complexes of different proteins, aggregates of the same protein, and/or nucleic acid(s).

In order to detect two or more proteins in a complex, the binding moieties of the multivalent proximity probes have specificity for two or more different proteins, bringing the multivalent proximity probes in proximity if the proteins have formed a complex by binding each other or by just being close to each other such as being situated in the same cell membrane. In this case, preferably three multivalent proximity probes are used.

Universal Probes

For indirect detection of a specific protein, a complex of said protein may be formed by first allowing two affinity reagents (for example an antibody pair) specific for their respective binding sites on the analyte to bind the analyte. And secondly, using a multivalent proximity probe pair specific for each of the two first affinity reagents to detect the proximity between these. If the first affinity reagents are in proximity they have bound the analyte, thereby detecting the analyte itself. A universal multivalent proximity probe pair can be used to detect several types of analytes, by being capable of binding the constant Fc-region of each of the analyte specific first affinity reagents.

In a second aspect, the invention relates to a kit for detecting and quantifying one or more analyte(s) in solution, comprising two or more multivalent proximity probes comprising at least two binding moieties but preferably 2-100 binding moieties, with affinity for the analyte(s) and provided with a nucleic acid (reactive functionality) capable of interacting with each other. In a preferred embodiment, one nucleic acid associated with a proximity probe has a free 3' end and the other (associated with the other proximity probe) has a free 5' end which may be suited by ligation.

The ligation reaction is preferably assisted by hybridization to a common splint ligation template oligonucleotide.

In the kit, the binding moieties of the multivalent proximity probes are selected from an antibody, antibody fragment, protein, nucleic acid, such as an aptamer, soluble cell surface receptor, combinatorially derived protein from phage display or ribosome display, or combinations thereof.

In one embodiment of the kit, the binding moieties are biotinylated and the kit further comprises streptavidin-oligonucleotide conjugates which may or may not be associated with the binding moieties.

In the kit, the multivalent proximity probes are provided on a polymer backbone such as a polypetide, polynucleotide, polysacharide, organic polymer such as polyethylenglycol, or other flexible polymer, or combinations thereof.

The following components can optionally be added in the kit:

a ligase for joining the nucleic acids; and a splint oligonucleotide which hybridizes to each of the reactive nucleic acids in the multivalent proximity probe pair.

primers which hybridise to each of the nucleic acids suitable for PCR amplification.

A pair of first binding reagents, for example antibodies, specific for the analyte to which the multivalent proximity probes secondarily bind.

In one embodiment, the kit comprises a pair of, or a triplet of, streptavidin-oligonucleotide conjugates which can be combined with biotinylated binding moieties forming multivalent proximity probes for use as pairs or triplets where the oligonucleotides can interact forming a detectable product when in proximity.

In another embodiment the kit comprises several pairs, or triplets of, streptavidin-oligonucleotide conjugates where each conjugate pair, or triplet, can be combined with biotinylated binding moieties forming multivalent proximity probes where each pair, or triplet, gives rise to a unique nucleotide sequence upon proximity dependent interaction for simultaneous detection of many analytes.

In other aspects the invention is related to the use of the method and/or kit for the following uses:

screening for ligand/receptor interaction antagonists in a high throughput procedure, where the multivalent proximity probes are capable of detecting the complex between the ligand and receptor for competitive detection and/or quantification of a known or unknown analyte in solution which is capable of disrupting the proximity of the multivalent proximity probe pair.

for screening ligand candidates in large libraries for screening drug candidates in large libraries which are capable of disrupting the proximity of the multivalent proximity probe pair for detection of infectious agents.

BRIEF DESCRIPTION OF THE DRAWINGS

6.A) A cross linker has multimerised the binding moieties with the reactive nucleic acid linked to the cross linker. Tie reactive nucleic acid may also be attached to the binding moiety.

6.B) A nucleic acid based backbone polymer with the binding moieties coupled to the backbone and the reactive nucleic acids hybridized to the backbone by base pairing. The nucleic acid backbone polymer may be concatemeric.

6.C) A short oligonucleotide (10-100 nucleotides) has first been coupled to the binding moiety. The oligonucleotide carrying the binding moiety is linked to the nucleic acid polymer by base pairing. The reactive nucleic acid is also linked to the backbone by base pairing 6.D) A reactive nucleic acid has been coupled to the binding moiety forming a monovalent proximity probe. This reactive nucleic acid carrying the binding moiety has hybridized to a nucleic acid polymer (preferred between 2-100 repeated units) forming a multivalent proximity probe. The nucleic acid polymer can be substituted by an oligonucleotide with for example 2 hydridization sites for the reactive nucleic acid linked to the binding moiety forming a divalent proximity probe.

6.E) Example of a multivalent proximity probe where the backbone polymer is made of nucleic acid which not only selves as a polymer for multimerisation but also as the reactive nucleic acid (r). The binding moieties are attached via a conjugated linking oligonucleotide hybridised to the backbone nucleic acid.

6.F) Example of a multivalent proximity probe with a SELEX aptamer based binding moiety (composed of a specific nucleic acid sequence, n) included in the concatemeric nucleic acid backbone polymer with a reactive nucleic acid (m) linked to the backbone by nucleotide base pairing.

Figure 2:
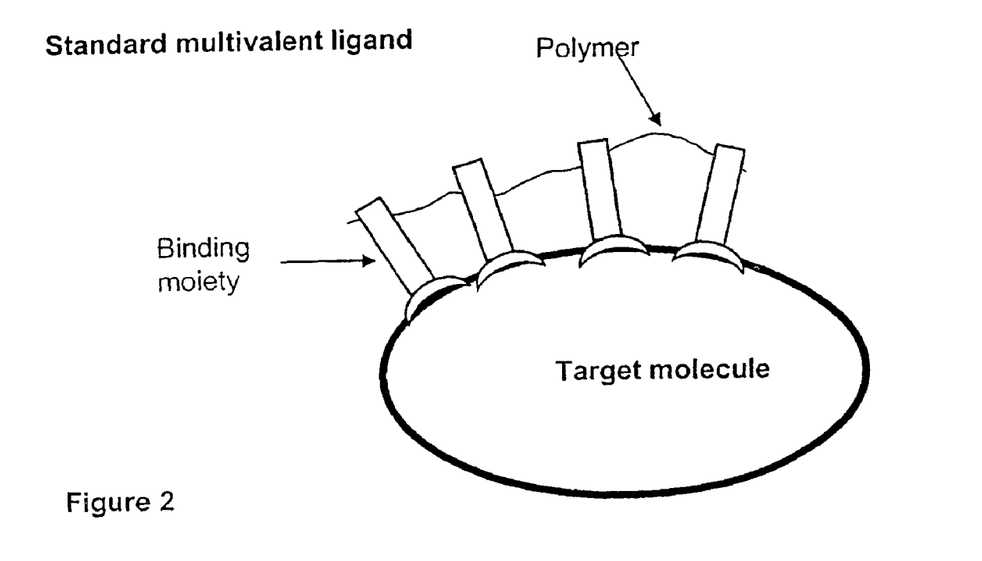
FIG. 2) Standard multivalent ligand of several binding moieties linked by a polymer bound to its target molecule with several binding sites for the binding moieties.

The standard concept of multivalency is often used to increase the affinity of a binder towards its target molecule (3). Here, several low affinity binders to one target molecule, with several binding sites, are multimerised for increased affinity. For example, this can be accomplished by covalently coupling several binders to a polymeric and flexible "backbone" producing a standard multivalent ligand, FIG. 2. The stabilisation of a multivalent complex results from the fact that an individual dissociated binder in a multivalent complex will quickly reassociate since the binder will remain in close proximity provided by the other remaining bindings. The reassociation rate in multivalent ligands is not diffusion dependent. This standard multivalency concept is used for increasing the affinity of binders to one molecule with several binding sites. The binding strength through multivalency can reach very high affinities (4).

Figure 3:
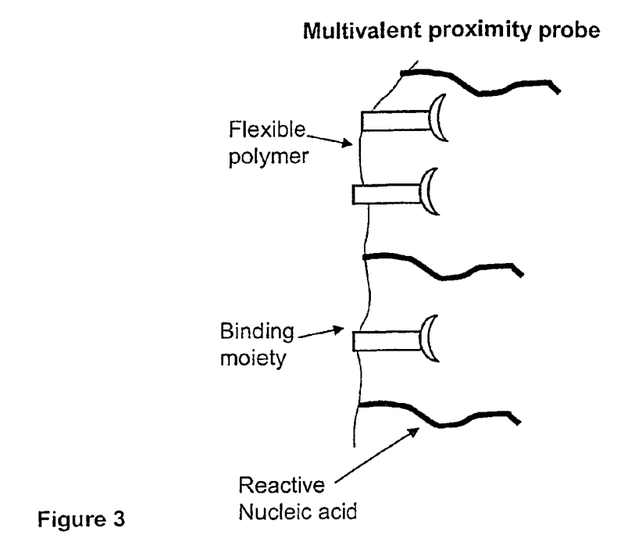
FIG. 3) Example of a multivalent proximity probe comprised of binding moieties, backbone flexible polymer, and reactive nucleic acid.

Another concept and use of multivalency is disclosed in this invention in regards to proximity probing. By incorporating several binding moieties in both members of a proximity probe pair, the affinity of the two multivalent proximity probes complexed with several copies of the target molecule is increased providing higher assay sensitivity. Such a multivalent proximity probe can be constructed by conjugating several binding moieties (such as antibodies or other) to a polymeric molecule along with the reactive nucleic acid, FIG. 3. Several copies of the reactive nucleic acids may also be coupled to the polymer backbone. The flexibility and the length of the linker between the ligands is important. The ligands need to be able to move relatively freely in order for the affinity to increase through multivalency. One binding event should not influence or sterically hinder the next binding. When choosing what type of backbone polymer to use, sufficient flexibility and spacing between the binding moieties should be considered.

DETAILED DESCRIPTION OF THE INVENTION

Figure 4:
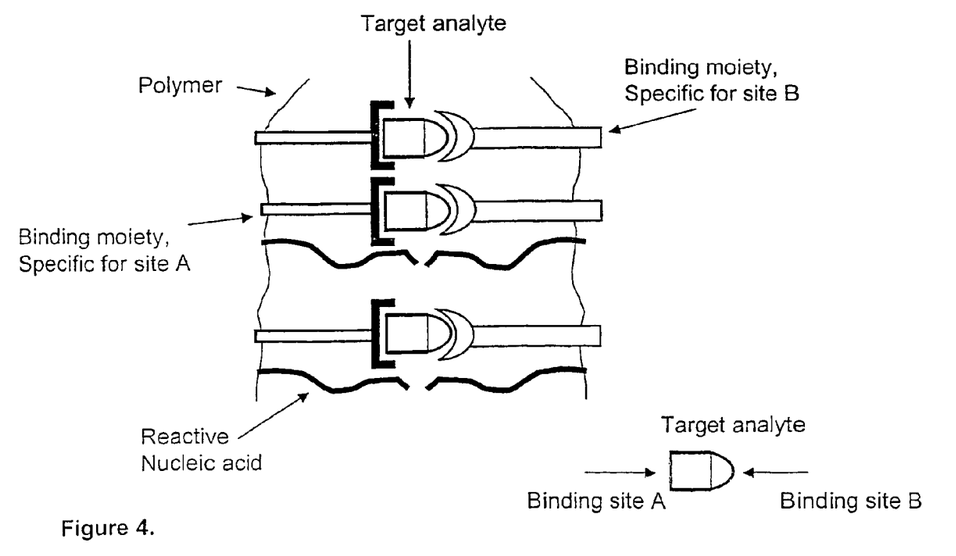
FIG. 4) Example of a multivalent proximity probe pair with several target analytes "sandwiched" in between the several binding moieties of the probes. The first multivalent proximity probe has binding moieties specific for site A on the analyte and the second multivalent proximity probe has binding moieties specific for site B on the analyte.

The binding of one multivalent proximity probe to a monomeric target analyte will not yield any increase in binding affinity since the dissociation of a binding will let the analyte to freely diffuse away from the multivalent proximity probe. But when both multivalent proximity probes with specificity to separate sites on the analyte are complexed with the analyte, several copies of the target analyte becomes "sandwiched" in between the multivalent proximity probes, FIG. 4. Since several targets are bound, cooperative effects greatly increase the binding strength of multivalent probe-target-multivalent probe complexes, increasing the assay sensitivity. A kind of "zippering" effect is achieved where each individual binding event stabilizes the others. At the start of the incubation of the multivalent proximity probe pair with the analyte sample, a multitude of complexes will form with various amounts of sandwiched targets. As the incubation time progresses, the most stable complex types will increase (those with several sandwiched targets)

Figure 5:
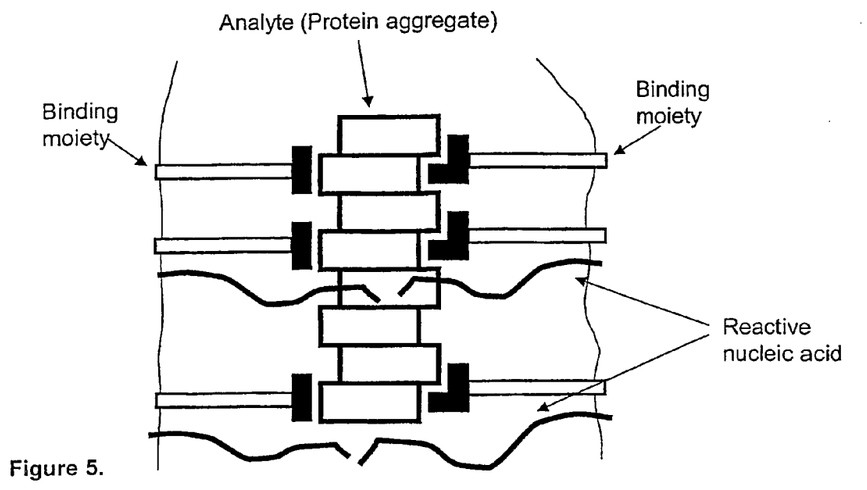
FIG. 5) Example of a multivalent proximity probe pair bound to an aggregated analyte such as a prion protein aggregate.

When detecting protein aggregates such as prion protein aggregates, the cooperative binding effect of a multivalent proximity probe will be even greater since several targets are also bound to each other further increasing the stability of the multivalent probe-target-multivalent probe complex, FIG. 5.

Many antibodies such as IgG are naturally divalent exposing two epitopes for antigen binding per antibody molecule.

Their ability to take advantage of this divalency when binding antigens depends on the flexibility of the hinge region linking the two epitopes and the geometric arrangement, which may sterically hinder the binding of one antigen to each epitope of an antibody (5). When making a multivalent proximity probe using antibodies they should at least contain two antibodies per probe with sufficient length of flexible backbone linker uniting the antibodies to ensure that the probe is capable of binding more than one target molecule.

When making a proximity probe by coupling a nucleic acid to a protein (such as an antibody) through conjugation one needs to purify the reaction product (antibody with nucleic acid) from the substrates (free nucleic acid and free antibody). This is important since any remaining free nucleic acid will increase the background noise in the assay and free binding moiety (antibody) will decrease the signal by occupying binding sites on target analytes. This purification can be made by several means such as ion exchange chromatography, gel filtration, or other. However, it is difficult to easily purify the reaction product since it resembles the substrates quite well. When making a multivalent proximity probe these physio-chemical differences, in especially size, will be greater between product and substrates making purification much easier by for example size exclusion chromatography or size exclusion membrane filtration by centrifugation.

Examples of Construction of Multivalent Proximity Probes

Several types of backbone polymers may be used to make multivalent proximity probes. Some examples are: polysaccharides such as dextran, polynucleotides such as Dna and Rna, polypeptides such as proteins, or organic polymers such as polyethylene glycol. The polymer must have some kind of reactive group to which the binding moiety and nucleic acid is coupled, covalently or non-covalently. For those skilled in the art, there are many synthesis chemistries to choose from and adapt when making a multivalent ligand. Some examples are: (6, 7, 8, 9, 10). The flexibility and the length of the linker separating the binding moieties is important. In order for the affinity to increase through multivalency, the ligands must be able to move as freely as possible. One binding event should not influence or hinder the next binding. When choosing what type of backbone polymer to use, sufficient flexibility and spacing between the binding moieties should be considered. The length of the reactive nucleic acids is also of importance since they need to be long enough to reach each other in order to interact when the proximity probes have bound the analyte. When using a polynucleotide sequence as backbone polymer, the nucleic acid can easily be attached by specific hybridization through base pairing. The nucleic acid based backbone polymer has some important advantages over reactive polymers such as amino modified dextran. The numbers and length of spacing between the attachment sites for the binding moieties can easily be controlled by using appropriate nucleic acid sequences in the backbone. The optimal distances between the binding moieties can then be optimised by varying the nucleic acid sequence composition of the backbone polymer by separating the hybridisation sites by more or fewer nucleotides. The flexibility of such a nucleic acid based polymer can also be controlled by varying the degree of double strandedness. Since dsDna has a more rigid and less flexible structure, the more the backbone is made double stranded the less flexible it is. The backbone nucleic acid can be made double stranded by simply hybridizing oligonucleotides.

Figure 6:
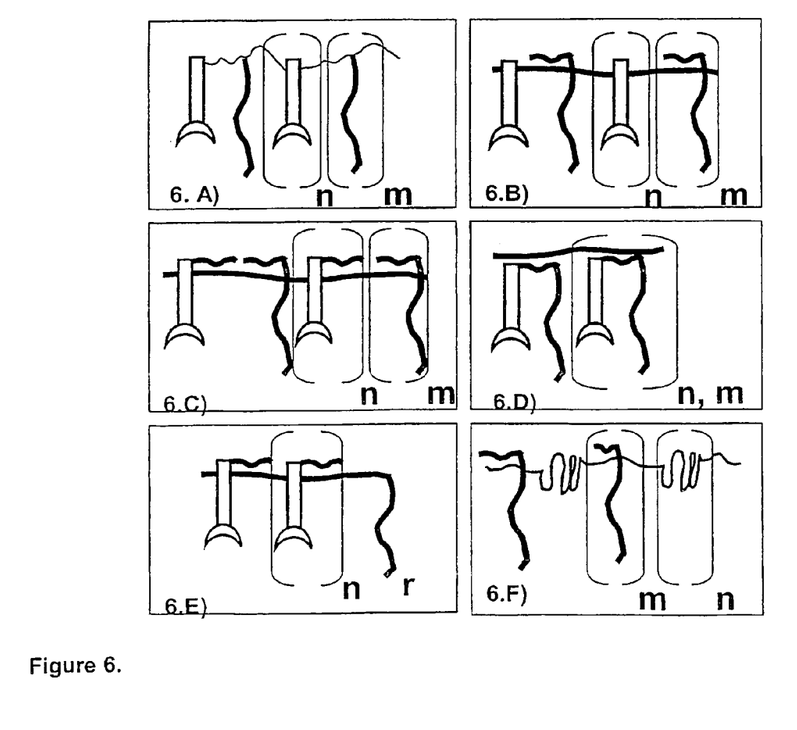
FIG. 6) Some examples of multivalent proximity probes. The symbol n is the number of additional repeated units of binding moiety resulting in multivalency, and is preferred between 1 and 100. 1 additional binding moiety, n=1, results in a divalent proximity probe with two binding moieties. The symbol m is the number of additional repeated units of reactive nucleic acid, and is preferred between 0 and 1000. 0 additional binding moieties results in a multivalent proximity probe with only one reactive nucleic acid.

FIG. 6 gives some examples of how multivalent proximity probes may be constructed. The examples may also be used in various combinations. A multivalent proximity probe is comprised of at least two binding moieties, both capable of binding a target molecule, and at least one reactive nucleic acid all linked together covalently or non-covalently.

The size of the multivalent proximity probe and the number of reactive nucleic acids and binding moieties can be varied with the length and number of coupling sites of the polymer to which they are linked. 2 to 100 binding moieties are preferred per multivalent proximity probe. The greater the number of binding moieties per probe, the greater the binding strength of the probe-target-probe complexes will be.

In some cases the polymer itself can contain the reactive nucleic acid and/or the binding moiety. FIG. 6.E shows an example of a multivalent proximity probe where the backbone nucleic acid polymer also is the reactive nucleic acid used for the proximity dependent interaction. Either one (5'- or 3'-) or both (5'- and 3'-) ends of each multivalent proximity probe backbone polymer take part in the proximity dependent interaction. If both ends are proximity dependently ligated, a circular nucleic acid is formed which may be amplified and detected by rolling circle amplification (11). The backbone nucleic acid polymer can itself comprise of the binding moiety when using selex derived aptamers which are target binding moieties composed of a specific nucleic acid sequence. The aptamer sequence can be concatemerically included in the polynucleotide polymer to which the nucleic acid is also bound by hybridization or covalent coupling, FIG. 6.F. Such a concatemeric polymer can be made by rolling circle replication (11) of a circular oligonucleotide containing the appropriate sequence elements (aptamer and reactive nucleic acid hybridization site).

During the construction of the multivalent proximity probes there will arise a multitude of products of varying ratios of binding moieties to reactive nucleic acid to backbone polymer due to less than quantitative coupling efficiencies and non-homogenous length of the backbone polymer. These complexes will be difficult to purify from one another resulting in a heterogeneous mixture of proximity probes. However, the most important purification that will improve assay performance is the removal of unlinked free binding moieties and unlinked free reactive nucleic acids. One may also affinity tag the backbone polymer for affinity purification construction products, for example by biotinylation and purification on an avidin resin.

The problem of remaining free binding moieties (capable of lowering signal) that where unable to be removed during the purification of the proximity probe is smaller with multivalent proximity probes compared to monovalent. This is the case, since the affinity of remaining free binding moieties, which are monovalent, will be lower compared to the multivalent proximity probe. They are thereby less able to compete for binding to the analyte and less likely to block the multivalent proximity probe from binding.

Specific Example of Construction of a Multivalent Proximity Probe

Described here, is the construction procedure of a multivalent proximity probe also shown in FIG. 6.D. A proximity probing reactive nucleic acid oligonucleotide is first coupled to the binding moiety, in this case an antibody. First, the antibody is derivatised with a 20-fold excess of SMPB (succinimidyl 4(p-maleimidophenyl) butyrate) in PBS buffer, providing a thiol-reactive maleimide functionality on the antibody. A thiol end-modified oligonucleotide is reduced using DTT and excess DTT is removed by size exclusion gel chromatography and the oligonucleotide is quickly added to the antibody in equimolar amounts. A covalent thio-ester bond is formed between the antibody and the oligonucleotide. This reactive oligonucleotide contains sequences for binding a polymeric backbone nucleic acid concatemer for multimerization and sequences for reaction with the other reactive oligonucleotide in the proximity probe pair and also sequences for amplification of the interaction product. Excess of unreacted oligonucleotide is removed by ammonium sulphate precipitation by adding 0.5 volumes of saturated ammonium sulphate and centrifugation. This precipitates the antibodies and antibody-oligonucleotide conjugates only. The precipitate is redissolved in PBS.

The concatemeric backbone oligonucleotide is added which contains two sequences each capable of binding by Watson-Click base pairing to one reactive oligonucleotide previously covalently linked to the antibody. The polymeric backbone oligonucleotide is added at sub equimolar amounts compared to the reactive oligonucleotide-antibody conjugate to ensure that two conjugates are hybridized to each backbone oligonucleotide. This backbone oligonucleotide carries a biotin label to enable purification on an avidin resin in order to remove excess of antibodies that do not carry the reactive nucleic acid by washing before eluting with excess of free biotin. The divalent proximity probe can now be used in a proximity probing assay along with its partner proximity probe constructed in the same fashion but containing an antibody specific for another site on the target molecule and another reactive nucleic acid sequence capable of proximity dependent interaction with the first by for example ligation.

Construction of Multivalent Proximity Probes Through Streptavidin Networks

The following strategies for constructing multivalent proximity probes capable of detecting insulin and VEGF, vascular endothelial growth factor (see below) are examples and can be used for detecting any macromolecule by using other antibodies with specificity for the desired target molecule. Other affinity reagents than antibodies can also be used such as DNA/RNA aptamers, antibody fragment, protein, soluble cell surface receptor, combinatorially derived protein from phage display or ribosome display or combinations thereof.

Figure 7:
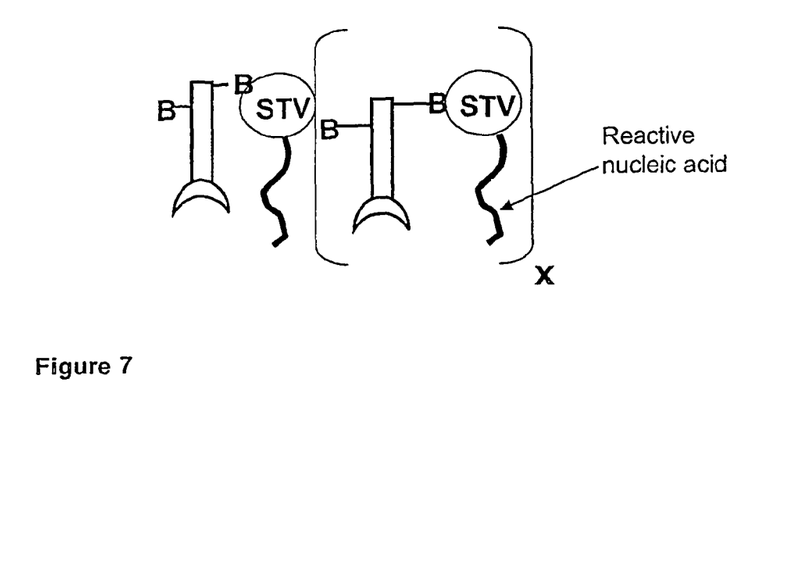
FIG. 7) A multivalent proximity probe based on streptavidin-biotin interactions. A multiply biotin labeled antibody bound by streptavidin-DNA conjugates. X is the number of additional repeated units of binding moiety and streptavidin-oligonucleotide conjugate and is preferred between 1 and 100.

Streptavidin is a tetrameric protein capable of binding four biotin molecules with very high affinity and is widely used in coupling technologies. Biotin can be coupled to various biomolecules such as DNA, RNA, and proteins. And with the addition of streptavidin, these biomolecules can be multimerised. Streptavidin preferentially binds two biotinylated molecules per streptavidin. If the biomolecule contains several biotins highly multivalent structures can form. This requires the appropriate ratios of streptavidin and the biotinylated molecules in the coupling incubation. The efficiency of multimerisation in regards to the molar ratios of reagents has been studied extensively (12,13,14). Between a multiply biotin labeled substrate and a streptavidin-oligonucleotide conjugate a ratio of 2:1 (substrate:streptavidin) was found to make supramolecular structures, also called aggregates (12). When making multivalent proximity-probes using this principal strategy, care must be taken to use the proper molar ratios which result in multimerisation and the generation of a reagent with increased sensitivity in proximity probing, FIG. 7 shows a schematic drawing exemplifying a multivalent proximity probe made with biotin-streptavidin interactions. After the coupling incubation many products are formed of various size and valency. A prefered product may be isolated by separation techniques such as gel filtration. In the example below no such separations where done.

A pair of multivalent proximity probes with antibody binding moeities was constructed by biotinylating two monoclonal antibodies with NHS-ester chemistry (Pierce) using excess biotinylation reagent resulting in several biotin molecules per antibody. These two antibodies (named 1 and 2) bind to two respective sites on human insulin.

Two conjugates between streptavidin and two different reactive oligonucleotides were constructed by coupling a thiol modified oligonucleotide to a maleimide derivatised streptavidin (Sigma). The first streptavidin-oligonucleotide conjugate contained: streptavidin-thioester -TTTCATCGC-CCTTGGACTACGACTGACGAAC-CGCTTTGCCTGACTGATCGCTA AATCGTG-3'-OH (SEQ ID NO.1). The second streptavidin-oligonucleotide conjugate contained: 5'P -TCGTGTCTAAAGTCCGTTAC-CTTGATTCCCCTAACCCTCTTGAAAAATTCGGC ATCGGTGA-thioester-streptavidin (SEQ ID NO.2). Proximity between these two oligonucleotides can be analysed in a proximity-probing protocol using the following oligonucleotides: Ligation template oligonucleotide, "splint" (TACTTA-GACACGACACGATTTAGTTT) (SEQ ID NO.3) PCR primer Frw (CATCGCCCTTGGACTACGA) (SEQ ID NO.4) PCR primer Rev (GGGAATCAAGGTAACG-GACTTTAG) (SEQ ID NO.5) TaqMan probe, Vic and Tamra labeled (TGACGAACCGCTTTGCCTGACTGA) (SEQ ID NO.6)

Figure 8:
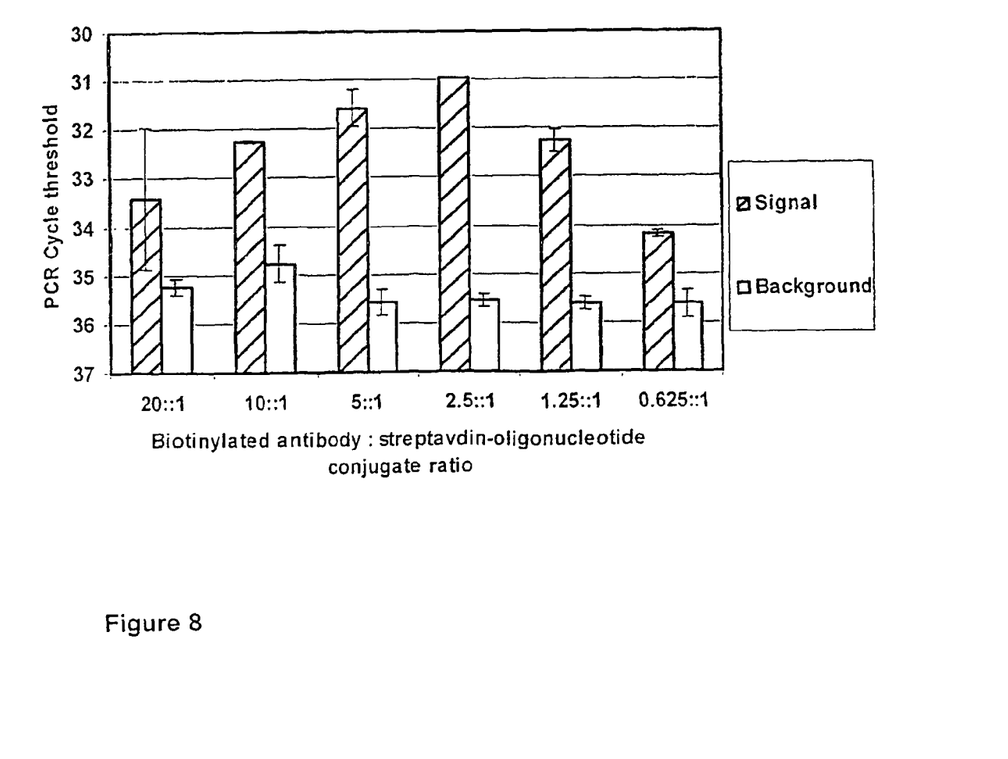
FIG. 8) Results from multivalent proximity-probing detection of human insulin using two monoclonal antibodies each constructed into multivalency through biotin-streptavidin networks. Various coupling ratios between multiply biotinylated antibody and streptavidin-oligunucleotide conjugate. Highest signal is achieved at 2.5:1 coupling ratios where aggregates of high multivalency is formed. A low Cycle threshold value indicates a high number of ligation events between the reactive nucleic acids corresponding to high efficiency of insulin detection. Signal indicates with insulin and background without insulin. Results are shown with standard deviations.

By incubating the biotinylated antibody 1 with the first streptavidin-oligonucleotide conjugate and antibody 2 with the second conjugate in different molar ratios, an optimal ratio was found where the insulin detection sensitvity was highest, FIG. 8. 10 nM streptavidin conjugate was preincubated with the biotinylated antibody at varied concentrations, then diluted to 100 pM streptavidin concentration in PBS buffer with 0.1% BSA, poly-A DNA, and 2.5 µM free biotin, which quenches any remaining streptavidin conjugates. This quenching disables the two different streptavidin conjugates to bind to one and the same biotinylated antibody which would generate target independent proximity. The two antibody-streptavidin complexes were then mixed together in a 5 µL volume with the sample containing either 0.2 nM insulin or no insulin.

After a 30 minute incubation at 37° C. a 45 µL mix containing all reagents required for ligation and amplification with real-time detection was added. After this addition, the sample contained 50 mM KCl, 10 mM Tris-HCl pH 8.3, 3.5 mM $MgCl_2$, 0.4 units T4 DNA ligase (Amersham Biosciences), 400 nM ligation template oligonucleotide, 80 µM ATP, ROX internal fluorescence standard, 0.2 mM dNTPs, 0.5 µM primers, 50 nM TaqMan probe, and 1.5 units AmpliTaq Gold polymerase (ABI). The samples were run in an ABI 7000 with temperature cycling; 95° C. for 10 minutes and then 95° C. 15 seconds and 60° C. 60 seconds, repeated 45 times.

One could anticipate that the decrease in signal at higher molar incubation ratios is due to free antibodies blocking the functional proximity probes from binding the target insulin, FIG. 8. However, the decrease in signal observed with molar ratios of biotinylated antibody higher than 2.5:1 is instead a result of the formation of suboptimal reagents in the incubation of the streptavidin conjugate and the biotinylated antibody. This is proved in an additional experiment where the 2.5:1 incubation was quenched with free biotin and then supplemented with excess biotinylated antibodies. This did not have as significant a negative effect on the signal as when incubating in high molar ratios (not shown). The finding of the 2.5:1 ratio to be optimal for construction of multivalent proximity probes is consistent with the literature where 2:1 ratios yielded multimeric products (12). Further increases in sensitivity can be achieved by purifying the multimeric proximity probes before use by, for example, gel filtration.

In a separate experiment, a polyclonal anti-VEGF antibody batch was incubated with the first streptavidin conjugate in one vessel and with the second streptavidin conjugate in another vessel at ratios generating multivalency of the two proximity probes. These incubations where diluted and quenched with free biotin and used for detection of VEGF using the same protocol as for insulin detection. The detection is enabled by the polyclonal antibody batch consisting of several antibodies of various specificities towards VEGF capable of binding at different sites on VEGF. Polyclonal antibodies are easily raised against proteins and the need for only one antibody batch simplifies the generation of reagents for proximity probing.

The invention claimed is:

1. A kit comprising:
a pair of different streptavidin-oligonucleotide conjugates, each of said conjugates comprising an oligonucleotide and a streptavidin that is not associated with a biotinylated molecule, wherein one of the conjugates of said pair has an oligonucleotide with a free 3' end and the other member of the conjugates of said pair has an oligonucleotide with a free 5' end; and
a splint ligation template oligonucleotide having a sequence that can hybridize to both of the oligonucleotides of said pair of conjugates when the oligonucleotides of said pair of conjugates are in proximity to one another and in contact with said splint ligation template oligonucleotide.

2. The kit according to claim 1, further including components for allowing said oligonucleotides to ligate to one another to form a detectable new nucleic acid product when the oligonucleotides of said conjugates are in proximity to one another and in contact with said splint ligation template oligonucleotide.

3. The kit according to claim 2, wherein said new nucleic acid product is detectable by amplification.

4. The kit according to claim 1, further comprising a pair of PCR primers, one of said pair of PCR primers having a sequence that can hybridize to the oligonucleotide of one of said pair of conjugates and the other member of said pair of PCR primers having a sequence that can hybridize to the oligonucleotide of the other member of said pair of conjugates.

5. The kit according to claim 4, further including a polymerase.

6. The kit according to claim 1, further comprising a ligase enzyme.

7. The kit according to claim 1, further comprising biotinylated binding moieties that are not associated with said pair of different streptavidin-oligonucleotide conjugates.

8. The kit according to claim 7, wherein each of said biotinylated binding moieties has an affinity for an analyte and at least two of said biotinylated binding moieties are capable of binding to different sites on said analyte.

9. The kit according to claim 7, further comprising a pair of first binding reagents specific for an analyte, wherein each of said biotinylated binding moieties has an affinity for one of said pair of first binding reagents specific for an analyte.

10. A kit comprising:
a pair of different streptavidin-oligonucleotide conjugates, each of said conjugates comprising an oligonucleotide and a streptavidin that is not associated with a biotinylated molecule, wherein the oligonucleotide in one of said pair of conjugates is different from the oligonucleotide in the other member of said pair of conjugates;
a splint ligation template oligonucleotide having a sequence that can hybridize to both of the oligonucleotides of said pair of conjugates when the oligonucleotides of said pair of conjugates are in proximity to one another and in contact with said splint ligation template oligonucleotide; and
a pair of PCR primers, one of said pair of PCR primers having a sequence that can hybridize to the oligonucleotide of one of said pair of conjugates and the other member of said pair of PCR primers having a sequence that can hybridize to the oligonucleotide of the other member of said pair of conjugates.

11. The kit according to claim 10, further including a polymerase.

12. The kit according to claim 10, further including a ligase enzyme.

13. The kit according to claim 12, further including a polymerase.

14. The kit according to claim 10, further comprising biotinylated binding moieties that are not associated with said pair of different streptavidin-oligonucleotide conjugates.

15. The kit according to claim 14, wherein each of said biotinylated binding moieties has an affinity for an analyte and at least two of said biotinylated binding moieties are capable of binding to different sites on said analyte.

16. The kit according to claim 14, further comprising a pair of first binding reagents specific for an analyte, wherein each of said biotinylated binding moieties has an affinity for one of said pair of first binding reagents specific for an analyte.

17. The kit according to claim 10, further including components for allowing said oligonucleotides to ligate to one another to form a detectable new nucleic acid product when the oligonucleotides of said conjugates are in proximity to one another and in contact with said splint ligation template oligonucleotide.

18. The kit according to claim 17, wherein said new nucleic acid product is detectable by amplification.

* * * * *

SEQUENCE LISTING

```
<160> NUMBER OF SEQ ID NOS: 6

<210> SEQ ID NO 1
<211> LENGTH: 60
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (1)..(1)
<223> OTHER INFORMATION: Residue at position 1 is modified by a
      thioester-streptavidin moiety.

<400> SEQUENCE: 1
tttcatcgcc cttggactac gactgacgaa ccgctttgcc tgactgatcg ctaaatcgtg    60

<210> SEQ ID NO 2
<211> LENGTH: 61
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (61)..(61)
<223> OTHER INFORMATION: Residue at position 61 is modified by a
      thioester-streptavidin moiety.

<400> SEQUENCE: 2
tcgtgtctaa agtccgttac cttgattccc ctaaccctct tgaaaaattc ggcatcggtg    60
a                                                                    61

<210> SEQ ID NO 3
<211> LENGTH: 26
<212> TYPE: DNA
<213> ORGANISM: Artificial
<220> FEATURE:
<223> OTHER INFORMATION: synthetic

<400> SEQUENCE: 3
tacttagaca cgacacgatt tagttt                                         26

<210> SEQ ID NO 4
<211> LENGTH: 19
<212> TYPE: DNA
<213> ORGANISM: Artificial
<220> FEATURE:
<223> OTHER INFORMATION: synthetic

<400> SEQUENCE: 4
catcgccctt ggactacga                                                 19

<210> SEQ ID NO 5
<211> LENGTH: 24
<212> TYPE: DNA
<213> ORGANISM: Artificial
<220> FEATURE:
<223> OTHER INFORMATION: synthetic

<400> SEQUENCE: 5
```

```
gggaatcaag gtaacggact ttag                                              24
```

<210> SEQ ID NO 6
<211> LENGTH: 24
<212> TYPE: DNA
<213> ORGANISM: Artificial
<220> FEATURE:
<223> OTHER INFORMATION: synthetic

<400> SEQUENCE: 6

```
tgacgaaccg ctttgcctga ctga                                              24
```